(12) United States Patent
Berndt et al.

(10) Patent No.: US 9,446,408 B2
(45) Date of Patent: Sep. 20, 2016

(54) SYSTEM FOR DISPENSING A SAMPLE INTO A BUFFER LIQUID

(71) Applicant: F. Hoffmann-La Roche AG, Basel (CH)

(72) Inventors: Peter Berndt, Basel (CH); Christof Fattinger, Blauen (CH); Roger Steiner, Allschwil (CH)

(73) Assignee: F. Hoffman-La Roche AG, Basel (CH)

( * ) Notice: Subject to any disclaimer, the term of this patent is extended or adjusted under 35 U.S.C. 154(b) by 0 days.

(21) Appl. No.: 14/426,360

(22) PCT Filed: Sep. 6, 2013

(86) PCT No.: PCT/EP2013/068474
§ 371 (c)(1),
(2) Date: Mar. 5, 2015

(87) PCT Pub. No.: WO2014/037506
PCT Pub. Date: Mar. 13, 2014

(65) Prior Publication Data
US 2015/0238966 A1    Aug. 27, 2015

(30) Foreign Application Priority Data

Sep. 6, 2012 (EP) .................................... 12183365

(51) Int. Cl.
*B01L 99/00* (2010.01)
*B01L 3/00* (2006.01)
*G01N 35/10* (2006.01)
*B01L 3/02* (2006.01)

(52) U.S. Cl.
CPC ................ *B01L 3/52* (2013.01); *B01L 3/0262* (2013.01); *B01L 3/0293* (2013.01); *B01L 3/502715* (2013.01); *G01N 35/1095* (2013.01);
*B01L 2200/027* (2013.01); *B01L 2200/0673* (2013.01); *B01L 2300/069* (2013.01); *B01L 2300/0838* (2013.01); *B01L 2300/0877* (2013.01); *B01L 2300/14* (2013.01); *B01L 2400/024* (2013.01); *B01L 2400/0406* (2013.01); *B01L 2400/0487* (2013.01); *Y10T 436/25625* (2015.01)

(58) Field of Classification Search
CPC ................ B01L 2400/0406; B01L 2300/0838
See application file for complete search history.

(56) References Cited

U.S. PATENT DOCUMENTS

| | | |
|---|---|---|
| 2002/0182749 A1 | 12/2002 | Singh et al. |
| 2003/0068646 A1 | 4/2003 | Singh et al. |
| 2005/0178801 A1 | 8/2005 | Lambrecht |
| 2005/0249641 A1 | 11/2005 | Blankenstein et al. |
| 2009/0020555 A1 | 1/2009 | Noda et al. |
| 2009/0182286 A1 | 7/2009 | Wolfson |

OTHER PUBLICATIONS

International Search Report and Written Opinion issued in PCT/EP2013/068474 on Jan. 24, 2014.

*Primary Examiner* — Paul Hyun
(74) *Attorney, Agent, or Firm* — Mintz Levin Cohn Ferris Glovsky and Popeo, P.C.

(57) ABSTRACT

A system for dispensing a sample into a buffer liquid includes a pressure chamber having pressure supply means for generating an overpressure within the pressure chamber. An inlet capillary supplies a buffer liquid to an outlet end arranged in the pressure chamber, and an outlet capillary discharges the buffer liquid from the pressure chamber. The outlet capillary has an inlet end in the pressure chamber facing the outlet end of the inlet capillary to form a capillary gap. A dispenser having a dispensing end is in the pressure chamber at the capillary gap to allow the sample at the dispensing end to be dispensed into the buffer liquid entering the outlet capillary inlet end. The pressure chamber includes a sample port that allows the dispenser to be moved into and out of the pressure chamber.

15 Claims, 6 Drawing Sheets

SYSTEM FOR DISPENSING A SAMPLE INTO A BUFFER LIQUID

RELATED APPLICATION

This application is a national stage application, filed under 35 U.S.C. §371, of International Application No. PCT/EP2013/068474 filed on Sep. 6, 2013, which claims priority to European Patent Application No. 12183365.1 filed on Sep. 6, 2012, the contents of which are hereby fully incorporated by reference.

The present invention relates to a system for dispensing a sample into a buffer liquid according to claim 1.

Dispensing biological samples containing biomolecules into a buffer liquid is a task that has to be performed in many applications. As an example, in the drug discovery process a large number of substances have to be screened to identify potential candidate substances for a drug and many tests have to be performed with such substances. For example, one of the questions of interest in the drug discovery process is whether a specific candidate substance binds to a specific target protein or enzyme. For that purpose, the candidate substance may be administered to a cell culture or to a tissue sample (tissue), and after a predetermined time it has to be analyzed whether or not the candidate substance is bound to the target protein or enzyme which is present in the tissue.

For performing this analysis, the substance must be retrieved from the tissue, either bound or not bound to the protein or enzyme. The tissue may be provided as a thin tissue slice arranged on a substrate, e.g. a glass plate. The substance, either bound or not bound to the protein or enzyme, must then be retrieved from the tissue. Different methods and techniques are known how the substance, either bound or not bound to the protein or enzyme, can be retrieved from the tissue slice.

The retrieved substance must then be analyzed as to whether or not it is bound to the target protein or enzyme. This can be performed by electro-spraying the substance into a mass spectrometer. Electrospraying is performed in particular in connection with biochemical or biological substances, since these substances contain macro-molecules which must be ionized and transferred to the vacuum of the mass spectrometer without these molecules getting destructed or damaged. The measurement result of the mass-spectrometer then reveals whether or not the substance is bound to the target protein or enzyme.

Electrospray ionization is a technique which is well-known in the art. A sample solution containing an analyte flows through a capillary tube made from glass or metal, and the outlet end of the capillary tube forms a very narrow tip. At least in the region of the tip the outer surface of the capillary tube is made of metal or is metallized to form an electrode. A counter-electrode is arranged distant to said electrode and a high voltage (typically between 1 kV and 5 kV) is applied between both electrodes and penetrates the solution. Through the electrophoretic movement of the ions, a predominant number of ions having the same polarity as that of the electrode accumulate at the tip. Charged droplets containing a predominant number of ions having the same polarity as the electrode are sprayed from the tip. As the solvent evaporates the droplets are getting smaller and the ions contained in the droplets move towards the surface of the droplets. As evaporation of the solvent proceeds and the size of the droplets decreases below a certain threshold (Rayleigh limit), the droplet explodes (Coulomb explosion) and the ions reach the mass spectrometer without solvent where they are detected and/or measured.

Typically, a mass spectrometry measurement includes a reference measurement of a known buffer liquid and a measurement of the liquid sample containing the analyte. The buffer liquid may contain reference substances that serve the purpose of unambiguously identifying target substances. Apart from serving as a reference, this has the additional advantage that it can be continuously supplied to prevent the capillary tube from drying out from the tip of which the buffer liquid or the liquid sample is sprayed. Obtaining the liquid sample is typically performed using high pressure liquid chromatography (HPLC) in which the various components contained are separated. However, this requires separation columns and/or capillary supply tubes of significant lengths. The supply of either buffer liquid or liquid sample to the capillary spray tube is then performed using specific mechanical valves sold under the trademark Rheodyne® which are available from IDEX Health and Science Corporation, Washington State, U.S.A. These valves comprise different ports which can be selectively connected by a rotatable selector, so that in a first position of the rotatable selector a buffer liquid inlet port, through which the buffer liquid is supplied, is connected to a capillary spray tube outlet port to which a capillary tube leading to the capillary spray tube may be connected. The liquid sample is provided in a loop comprising a capillary tube and a channel portion within the valve. In the first position of the rotatable selector, the liquid sample is pumped through this loop. In order to introduce the liquid sample into the flow of buffer liquid, the selector is rotated from the first position to a second position. In this second position, the buffer liquid inlet port of the valve is connected to an inlet end of the channel portion of the valve in which a small amount of the liquid sample is contained. The outlet end of the channel portion in which the said small amount of liquid sample is contained is connected to the capillary spray tube outlet port of the valve. Thus, the small amount of liquid sample is supplied from the loop to the capillary tube leading to the capillary spray tube, preceded by and followed by buffer liquid, respectively. Accordingly, after the small amount of liquid sample has been electro-sprayed it is again buffer liquid which is electro-sprayed from the outlet end of the capillary spray tube. The rotatable selector can then be returned to the first position, and the capillary loop can be rinsed and filled with another liquid sample.

Since the buffer liquid and the liquid sample are supplied with high pressure, the switching of the rotatable selector from the first position to the second position and vice versa must be liquid-tight and must withstand the high pressure. To fulfil these requirements, the switching takes place between a polymeric rotor seal and a ceramic stator face. While the afore-mentioned Rheodyne®-valves are capable of performing such switching, the switching action causes wear and even if some thousands or some ten thousands of switching actions may be reliably performed before the rotor seal must be replaced, it is necessary from time to time to replace the rotor seal. This is time consuming and makes these valves unsuitable for high throughput screening applications where millions of substances must be tested in short time intervals. Another disadvantage is that the valves and their replacement parts (e.g. the afore-mentioned seal)

A still further disadvantage is that comparatively large volumes of liquid sample must be provided in the loop comprising the capillary tube and the channel. This is particularly disadvantageous since in the case of biochemical or biological substances typically only very small volumes of the substances are available.

A still further disadvantage is that the length of the capillary spray tube connected to the capillary spray tube outlet port of the valve has a considerable length, since fittings are connected to the ports of the valve and the liquid is transported within a capillary tube arranged to extend through the fittings to the very narrow tip distant from the fittings, so that the entire length of the capillary spray tube cannot be neglected. This is disadvantageous in that the biochemical or biological samples introduced in the flow of buffer liquid are diluted with buffer liquid as they propagate through the long capillary tube. The longer the spray capillary tube is, the higher the probability that such dilution of small samples occurs. Accordingly, the longer the capillary is, the worse is the signal to noise ratio of the measurement of the mass spectrometer. Moreover, due to the comparatively large volumes of buffer liquid that must be sprayed from the tip before the next liquid sample can be sprayed, the time intervals between the spraying of two consecutive liquid samples (analytes) is comparatively long and may take some tenths of seconds or even more. This is too long for high throughput sampling of a large number of small liquid samples. In sum, the prior art suggests a comparatively coarse fluidic system which is coupled to a very small electrospray ionization tip at the inlet port of a mass spectrometer.

A state of the art apparatus is disclosed in US 2009/0020555 A1. The apparatus allows for transporting or dispensing liquid objects from a first transport pipe into a second transport pipe which are separated by an air gap. A pressure chamber is suggested to surround the air gap. However, a pressure loss occurs in the pressure chamber when a pipette is inserted into and later on removed from the pressure chamber.

Therefore, it is an object of the invention to provide a system for introducing or dispensing a sample into a buffer liquid which overcomes or at least greatly reduces the afore-mentioned disadvantages of prior art systems. In addition, the system for dispensing a sample into a buffer liquid shall be suitable for the supply of a sample containing large molecules, such as this is the case for biochemical or biological samples. Still further, the quantity of sample required should be reduced. Also, the system should be capable of being used in high throughput sampling applications such as high throughput screening, or molecular imaging of tissue slices.

In accordance with the invention, this object is achieved by a system for dispensing a sample into a buffer liquid as it is characterized by the features of the independent claim directed to the system. Advantageous embodiments of the system according to the invention are the subject of the dependent claims directed to the system.

In accordance with one embodiment of the invention, the system for dispensing a sample, in particular a liquid sample, into a buffer liquid comprises a pressure chamber having pressure supply means for generating an overpressure within the pressure chamber relative to a pressure outside the pressure chamber. The system further comprises an inlet capillary for supplying a buffer liquid to an outlet end of the inlet capillary. The outlet end of the inlet capillary is arranged in the pressure chamber. The system further comprises an outlet capillary for discharging the buffer liquid and/or the sample from the pressure chamber. The outlet capillary has an inlet end which is arranged in the pressure chamber in a manner such that the outlet end of the inlet capillary and the inlet end of the outlet capillary are facing each other to form a capillary gap. This allows the buffer liquid exiting the outlet end of the inlet capillary to cross the capillary gap and enter the inlet end of the outlet capillary. The system still further comprises a dispenser. The dispenser has a dispensing end which, during dispensing of the sample, is arranged in the pressure chamber at the capillary gap. For example, the dispenser may comprise a solid pin, a pipette, or any other suitable device. For example, the dispenser may have a solid tip with a flat surface at the dispensing end, or it can be a hollow dispenser comprising a channel having an opening at the dispensing end. This allows the sample adhering to or exiting from the dispensing tip to be dispensed from the dispensing end into the buffer liquid entering the inlet end of the outlet capillary. In case of a liquid sample the sample may form a liquid bridge to the buffer liquid entering the inlet end of the outlet capillary.

As already mentioned, the dispenser may comprise a solid pin with a flat, e.g. hydrophilic, surface at its dispensing end to which a liquid droplet adheres (so called pin tool), a pipetting tip, or any kind of hollow tip or column that is suitable for transportation of a sample from a sample plate or a tissue slice to the liquid bridge in the capillary gap. For example, the hollow tip or column can be filled with a gel, e.g. an agarose matrix. The gel may be loaded and unloaded with sample molecules by applying an electric field to it. The gel acts as an anticonvective medium during electrophoretic movement of the sample molecules into and out of the hollow tip or column by an electrical field that is applied to it. The electrical field in the tip or column changes polarity between loading of molecules into the gel from a sample and unloading them from the dispensing end to the buffer liquid entering the inlet end of the outlet capillary. In case of a liquid bridge formed between the inlet capillary and the outlet capillary, the sample may be unloaded into the liquid bridge formed in the capillary gap between the inlet capillary and the outlet capillary.

While in the following only cases are discussed in which a "capillary" is embodied as a capillary tube, the term "capillary" is to be understood to also comprise capillary channels of other types. As one example, a capillary may be formed by an open channel in a surface of a plate which is covered by a respective lid so as to form a closed capillary channel.

Generally, two main scenarios are conceivable of how the sample can be dispensed into the buffer liquid entering the inlet end of the outlet capillary.

In a first scenario, there is no continuously maintained bridge of buffer liquid spanning the gap between the outlet end of the inlet capillary and the inlet end of the outlet capillary. However, there is still some buffer liquid remaining at the inlet end of the outlet capillary in form of a droplet. As the sample is dispensed from the dispensing end of the dispenser, it also forms a droplet until the droplet of the buffer liquid present at the inlet end of the outlet capillary and the droplet of the sample present at the dispensing end form a liquid bridge. Also, the liquid bridge spanning the gap may be re-established by the sample dispensed. The surface pressure acting on the liquid surface prevents the liquid droplet at the inlet end of the outlet capillary and the liquid bridge from falling down. The sample is drawn into the outlet capillary, and is discharged from the outlet capillary due to the difference in pressure between the overpressure in the pressure chamber and the pressure outside the outlet capillary. The difference in pressure between the overpressure in the pressure chamber and the pressure outside the outlet end of the outlet capillary determines the flow rate of liquid through the outlet capillary.

In a second scenario, a liquid bridge of buffer liquid spanning the capillary gap between the outlet end of the inlet capillary and the inlet end of the outlet capillary is continuously maintained. As the sample is dispensed from the dispensing end of the dispenser it forms a droplet which then forms a liquid bridge with the continuously maintained bridge of buffer liquid spanning the capillary gap between the outlet end of the inlet capillary and the inlet end of the outlet capillary. The sample is drawn into the outlet capillary and is discharged from the outlet capillary due to the difference in pressure between the overpressure in the pressure chamber and the pressure outside the outlet capillary. The overpressure within the pressure chamber assists in restricting and controlling the liquid bridge spanning the gap between the outlet end of the inlet capillary and the inlet end of the outlet capillary. Also, as already mentioned the overpressure in the pressure chamber determines the flow rate through the outlet capillary.

Typically, the overpressure in the pressure chamber may be within a range of 0.1 bar to 2 bar (relative to the pressure outside the chamber, or outside the outlet end of the outlet capillary, respectively). Once a desired flow rate through the outlet capillary is achieved through an appropriate level of overpressure within the pressure chamber the liquid bridge spanning the gap between the outlet end of the inlet capillary and the inlet end of the outlet capillary can be controlled by reducing or increasing the flow rate of buffer liquid through the inlet capillary or by varying the overpressure in the pressure chamber.

The inlet end of the outlet capillary may be, for example, the inlet end of a capillary spray tube from which the buffer liquid and sample can be electro-sprayed into a mass spectrometer, as this has been already described above. Thus, with the system according to the invention it is possible to dispense only very small amounts of liquid more or less directly, that is to say at a location very close to the inlet, into the inlet end of the outlet capillary which, as mentioned above, may be the capillary spray tube. No loops are needed for providing the sample, but rather a very small amount of sample can be attained, for example by a dispenser as described above, which can then be introduced into the pressure chamber. The very small amount of sample attained by the dispenser can then be directly dispensed into the liquid bridge spanning the gap. Accordingly, the distance for the sample through the outlet capillary which may be the capillary spray tube is very short only, which is particularly advantageous with respect to large molecules of biochemical or biological samples, since these molecules tend to adhere to the capillary walls, and the probability that adherence occurs is the higher the longer the outlet capillary is. However, the more molecules contained in the sample reach the mass spectrometer the better is the signal to noise ratio. Accordingly, the system according to the invention is also advantageous in that it improves the signal to noise ratio in the mass spectrometer into which the sample and the buffer liquid are sprayed.

In some embodiments of the method, the limited dynamic range of the mass spectrometry detector may necessitate analytical separation steps before the injection of the analytes into the mass separator. This can be accomplished by dividing the outlet capillary and introducing separation media (typically implemented in form of a glass capillary whose internal walls are modified to function as a selective adsorption surface) between the part of the outlet capillary that faces the sampling gap and the part of the outlet capillary that faces the mass spectrometer. The buffer liquid that is continuously supplied to the outlet capillary may then have a time-varied composition (e.g. in order to form elution steps or gradients). This arrangement is not limited to a single separation media, but could conceivably consist of several orthogonal separation facilities.

The system according to the invention is suitable for use in high throughput sampling applications, since only very small volumes of sample have to be separated and sprayed, so that the spraying of such small volumes reduces the time until the next sample can be sprayed.

In accordance with one aspect of the system according to the invention, the pressure chamber may comprise a pressure-tight sample port adapted to allow the dispenser with the dispensing end to be moved into and out of the pressure chamber. This is an advantageous constructional embodiment of how a dispenser, such as a solid pin, a pipette or any other suitable device, can be inserted into and later on removed from the pressure chamber. It is particularly advantageous when large numbers of samples are to be measured as this is the case in a high throughput sampling applications, since for example a solid pin, a pipette or any other suitable device can rapidly attain a sample from the well of a micro-plate, and may then be rapidly introduced into the pressure chamber for dispensing the sample in the capillary gap. After dispensing, the solid pin, pipette or any other suitable device can be quickly removed from the pressure chamber through the pressure-tight sample port.

In accordance with a further aspect of the system according to the invention, the pressure-tight sample port may comprise a locking member having a passage therethrough. The locking member is movable between a first position in which the passage is arranged to allow the dispenser to pass into the pressure chamber and a second position in which the locking member locks the pressure chamber in a pressure-tight manner. This embodiment is advantageous since the locking member allowing pressure-tight access or preventing access to the pressure chamber can be constructed with low expense. For example, when the dispenser is formed as elongate solid pin, pipette or any other suitable device, the dispensing end may first be inserted through a seal while the locking member is arranged in the second position in which it locks the pressure chamber in a pressure-tight manner. As the solid pin, pipette or any other suitable device has passed the seal, the locking member may be moved from the second position to the first position in which the passage in the locking member allows the solid pin, pipette or any other suitable device to be moved into the pressure chamber. Once the sample has been dispensed from the solid pin, pipette or any other suitable device, the dispensing end is removed from the pressure chamber. This can be performed by removing the solid pin, pipette or any other suitable device until the dispensing end has been completely retracted through the passage while the dispensing end is still surrounded by the seal. The locking member is then moved from the first position to the second position in which it closes the pressure chamber in a pressure-tight manner. The solid pin, pipette or any other suitable device can then be completely retracted through the seal with the pressure chamber remaining closed in a pressure-tight manner.

As has already been indicated, in accordance with a further aspect of the system according to the invention the system may comprise a motor for moving the locking member from the first position to the second position and vice versa. Moving the locking member with the aid of a motor is preferred because the movement of the locking member can be performed in a very short time, for example within some hundred milliseconds or even faster, and at the same time vibrations or shocks to the system can be substantially or even completely avoided.

In accordance with another aspect of the system according to the invention, the dispenser comprises a channel and a dispensing opening arranged at the dispensing end. The dispensing opening is in communication with the channel to allow for dispensing of the sample through the dispensing opening. The channel may either be empty (such as in a conventional pipette) or may be filled with a chromatographic material, e.g. an agarose gel, as this has been described above. A so embodied dispenser allows for an easy and quick intake of the sample into the channel and also allows for an easy and quick dispensing of the sample through the dispensing opening.

In accordance with another aspect of the system according to the invention, the system may further comprise an inlet capillary holder and an outlet capillary holder for positioning the outlet end of the inlet capillary and the inlet end of the outlet capillary aligned with one another within the pressure chamber. The outlet end of the inlet capillary and the inlet end of the outlet capillary may be aligned with an accuracy in the range of typically +/−0.02 mm to +/−0.1 mm. By way of example, the capillary holders may be screwed into threaded holes provided at opposite sides of the pressure chamber. Additionally, the holder may be adapted to adjust the axial distance of the ends of the capillary tubes facing each other.

In accordance with a still further aspect of the system according to the invention, the pressure chamber may comprise a window which is arranged such that the outlet end of the inlet capillary, the inlet end of the outlet capillary, the dispensing end of the dispenser, and the capillary gap are visible. Thus, it is possible to control the alignment, the distance of the ends of the capillary tubes, the formation and maintenance of the liquid bridge spanning the gap, etc., as will be explained in the following.

In accordance with another aspect of the system according to the invention, the system may further comprise a camera for taking an image at least of the capillary gap and a control unit adapted to analyze the image taken by the camera to automatically control the pressure supply means and/or the supply of buffer liquid through the inlet capillary. The image analysis allows a real-time control of the liquid bridge spanning the capillary gap so that the fluid bridge can be established and maintained by adjusting the overpressure within the chamber based on an analysis of the captured images. Also, it allows to exactly position the outlet end of the inlet capillary and the inlet end of the outlet capillary relative to one another. The same holds for the dispenser, the dispending end of which can be exactly positioned with the aid of an analysis of the captured images.

In accordance with a further aspect of the system according to the invention, the pressure chamber may comprise a closable drain arranged in fluid communication with the capillary gap. Generally, the location of such drain is not limited to a certain portion of the pressure chamber. However, in case liquid inadvertently does not enter the inlet end of the outlet capillary (for example in case the overpressure within the pressure chamber is too small) it may fall down to the bottom of the pressure chamber due to gravity. Accordingly, the preferred location for such drain is below the capillary gap at the bottom of the pressure chamber. In addition, the drain allows purging of the pressure chamber with the aid of a stream of a purging gas flowing through the pressure chamber and out of the chamber through the said drain. Such drain may be simply embodied as an opening that can be closed and opened.

In accordance with a further aspect of the system according to the invention, the pressure supply means may comprise an overpressure source and a supply channel which is in fluid communication with both the overpressure source and the pressure chamber for introducing a pressurized gas into the pressure chamber. In addition, the pressure supply means may comprise a pressure drain for allowing pressurized gas to be discharged from the pressure chamber. The pressure drain may comprise a discharge channel and a discharge valve. The discharge channel is in fluid communication with both the pressure chamber and the discharge valve so as to establish a constant difference between the pressure within the pressure chamber and the pressure outside the pressure chamber. The difference in pressure typically is in the range of 0.1 bar to 2 bar. The main purpose of the pressure supply means, apart from controlling the liquid bridge spanning the gap, is to control the flow rate through the outlet capillary. The flow rate through the outlet capillary is directly related to the pressure difference between the overpressure inside the pressure chamber and the pressure outside the outlet capillary. A well-defined pressure leak at the pressure drain may assist in precisely controlling and maintaining the overpressure within the pressure chamber.

In accordance with a further aspect of the system according to the invention, the inlet capillary and the outlet capillary may have an inner diameter in the range of 5 μm to 100 μm, in particular in the range of 5 μm to 50 μm, and an outer diameter in the range of 50 μm to 500 μm. The outer diameter is always larger than the inner diameter. It is to be noted that this range is a preferred range only. The optimum width of the gap between the outlet end of the inlet capillary and the inlet end of the outlet capillary is in the range of the outer diameter of the inlet and outlet capillaries. Accordingly, as the outer diameter of the capillaries is in the specified range, the volume of liquid spanning the capillary gap can be kept small, in particular within the range of one nanoliter or less to some ten nanoliters. This is particularly advantageous when combined with the subsequently discussed aspect of a further embodiment of the invention.

In accordance with a still further aspect of the system according to the invention, the outlet capillary may have a length in the range of 10 mm to 50 mm. As mentioned, a short length of the outlet capillary is particularly advantageous in that it avoids adherence of large molecules, which are typically contained in biochemical or biological samples, to the inner walls of the outlet capillary. On the other hand, the outlet capillary must be mounted to the pressure chamber, preferably with the aid of a capillary holder, and it must be possible to apply a high voltage to the outlet capillary for the purpose of electro-spraying. Therefore, although the length of the outlet capillary is to be kept short, it must have a certain minimum length in order for it to be capable of complying with the requirements.

Alternatively, in accordance with a still further aspect of the system according to the invention, the outlet capillary may include sections of materials whose inner surfaces allow for the selective adsorption of parts of the sampling materials. Typically, such materials include reverse phase separation media or cationic or anionic sorption media.

In accordance with a further aspect of the system according to the invention, the inlet capillary and/or the outlet capillary is made from a fused silica, glass or polytetrafluoroethylene (Teflon®) or metal such as stainless steel or gold or platinum. These materials have shown to be suitable for the intended purpose. Advantageously, in case the capillaries are made from a hydrophilic material, the outer surfaces of the capillaries can be coated with a hydrophobic material such as Teflon® AF to avoid that liquid wets the outer surfaces of the capillaries while the end surfaces of the capillaries remain uncoated. The coating may be a thin layer having a thickness of e.g. 10 nm.

Similarly, the outer surface of the dispenser can be coated with such thin layer of Teflon® AF material for the same reason.

In accordance with a further aspect of the system according to the invention, the outlet capillary may have a tapered outlet end. The outlet capillary at least at the tapered outlet end is provided on its outer surface with metal. The outlet capillary is further electrically isolated against the pressure chamber and the outlet capillary holder, respectively. The system further comprises a voltage electrode arranged in electrical contact with the outlet end of the outlet capillary for applying a voltage to the metal provided on the outer surface of the outlet capillary at the tapered end thereof. This embodiment is particularly directed to an embodiment in which the outlet capillary is the short capillary for electrospraying the sample and/or buffer liquid into a mass spectrometer.

Another aspect of the invention relates to a method for dispensing a sample into a buffer liquid, the method comprising the steps of:
  providing a system according to the invention as it is described above for dispensing a sample,
  generating an overpressure within the pressure chamber,
  producing a buffer liquid flow through the outlet end of the inlet capillary into the inlet end of the outlet capillary,
  controlling the overpressure within the pressure chamber such that the difference between the pressure in the pressure chamber and the pressure outside the pressure chamber is constant to establish a constant flow rate in the outlet capillary, and
  dispensing a sample through the dispensing end of the sample dispenser to form a liquid bridge to the buffer liquid entering the inlet end of the outlet capillary.

In accordance with still another aspect of the method according to the invention, a capillary gap bridge of buffer liquid is continuously maintained between the outlet end of the inlet capillary and the inlet end of the outlet capillary. The step of dispensing the sample through the dispensing end of the dispenser comprises dispensing the sample into the continuously maintained capillary gap bridge of buffer liquid. The advantages of embodiments of the method according to the invention correspond to those already mentioned when discussing the system according to the invention.

Further advantageous aspects of the invention become apparent from the following description of embodiments of the invention with reference to the accompanying drawings in which.

Figure 1:
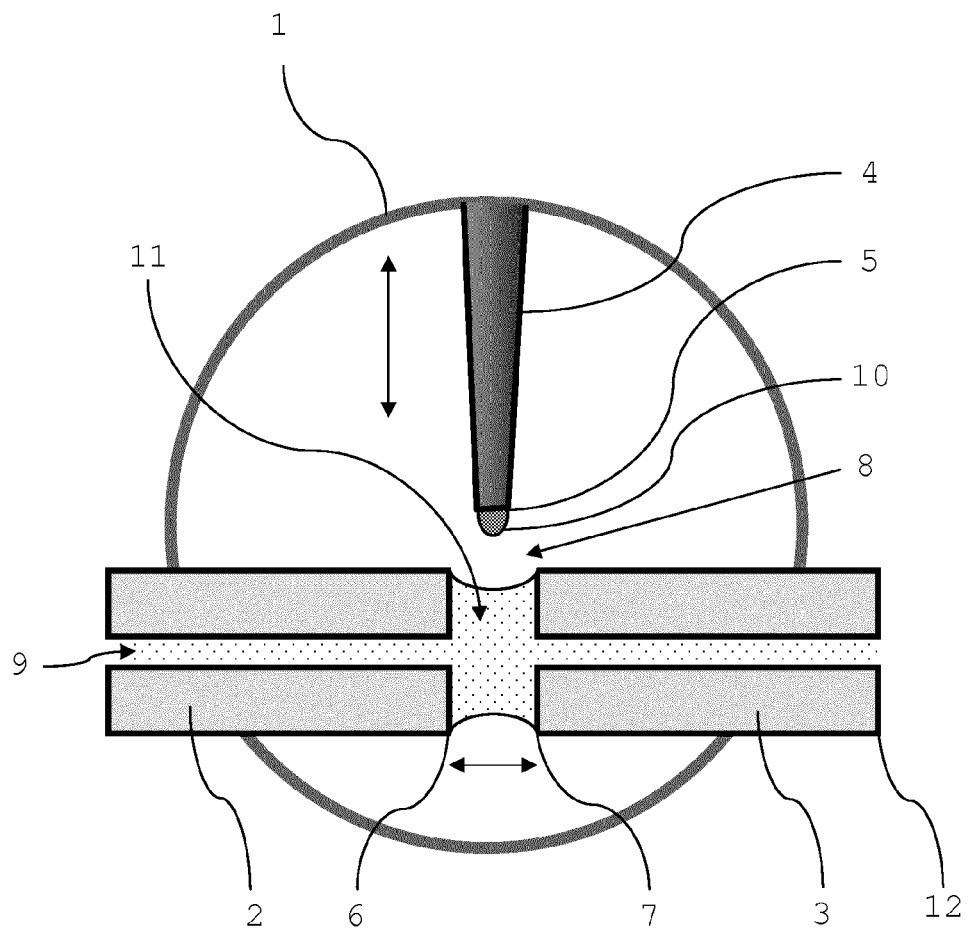
FIG. 1 shows a side view of an embodiment of the system according to the invention comprising an inlet capillary, an outlet capillary, and a dispenser, arranged within a pressure chamber.
Figure 2:
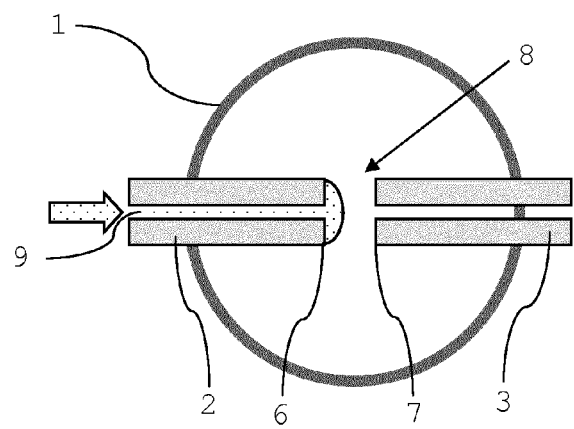
FIG. 2 shows the embodiment of the system of FIG. 1 without the dispenser, at the beginning of the formation of a capillary gap bridge of buffer liquid.
Figure 3:
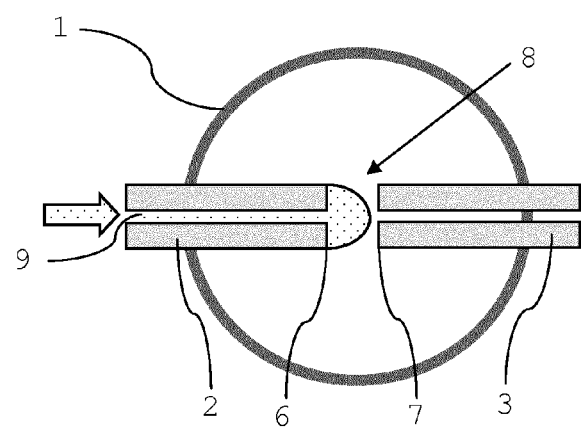
FIG. 3 shows the embodiment of the system of FIG. 2 during progression of the formation of the capillary gap bridge of buffer liquid.
Figure 4:
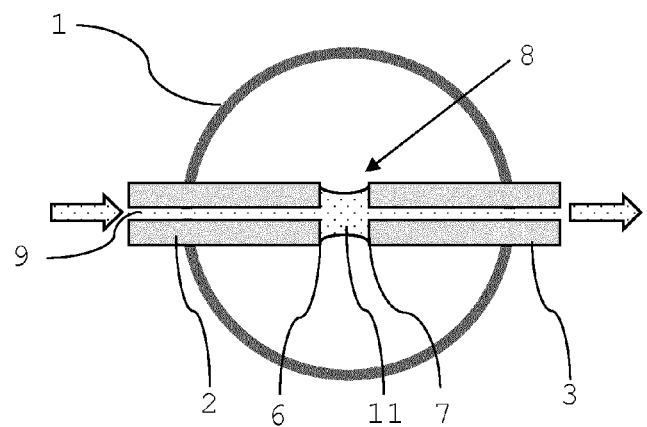
FIG. 4 shows the embodiment of the system of FIG. 2 and FIG. 3 with the capillary gap bridge being formed, so that a bridge of buffer liquid spans the capillary gap between the inlet capillary and the outlet capillary.
Figure 5:
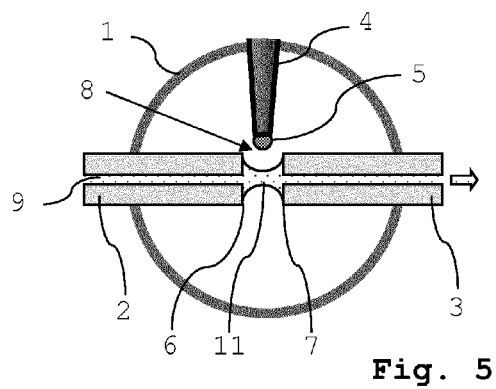
FIG. 5 shows the embodiment of the system of FIG. 1 at the beginning of the dispensing of the sample into the capillary gap bridge of buffer liquid in accordance with a first embodiment of the method according to the invention.
Figure 6:
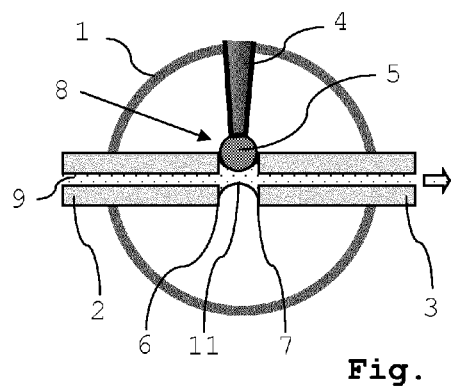
FIG. 6 shows the embodiment of the system of FIG. 5 during dispensing of the sample into the capillary gap bridge of buffer liquid.

FIG. 1 shows a first embodiment of a system for dispensing a sample into a buffer liquid 9 comprising a pressure chamber 1, an inlet capillary 2 and an outlet capillary 3, as well as a dispenser 4. As already mentioned further above, in the following embodiments the "capillary" is embodied as a capillary tube without being limited thereto. A buffer liquid 9 is supplied through the inlet capillary 2 to an outlet end 6 of the inlet capillary 2. This outlet end 6 of the inlet capillary 2 is arranged inside the pressure chamber 1. The outlet capillary 3 has an inlet end 7 which is arranged in the pressure chamber 1 in a manner such that the outlet end 6 of the inlet capillary 2 and the inlet end 7 of the outlet capillary 3 are facing each other. Thus, a capillary gap 8 is defined between the inlet capillary 2 and the outlet capillary 3, or to be more precise, between the outlet end 6 of the inlet capillary 2 and the inlet end 7 of the outlet capillary 3. The buffer liquid 9 flows through the inlet capillary 2 and forms a droplet at the outlet end 6 of the inlet capillary 2, as this is shown in FIG. 2. Further supply of buffer liquid through the inlet capillary 2 results in growing of the droplet at the outlet end 6 of the inlet capillary 2, as this is shown in FIG. 3, until the droplet contacts the inlet end 7 of the outlet capillary 3. A liquid bridge 11 then forms which spans the capillary gap 8, as this is shown in FIG. 4. Due to the overpressure within the pressure chamber 1 relative to the pressure outside the pressure chamber 1, or to be more precise relative to the pressure outside the outlet end 12 (see FIG. 1) of outlet capillary 3, the buffer liquid 9 that enters the outlet capillary 3 is discharged from the outlet end 12 of the outlet capillary 3. The flow rate through the outlet capillary 3 is determined by the said pressure difference. That is to say, a constant flow rate through the outlet capillary 3 can be achieved by a constant pressure difference.

Once the capillary gap bridge 11 of buffer liquid has been established, it is continuously maintained. Maintenance of the capillary gap bridge 11 can be controlled by controlling the flow rate of the buffer liquid supplied through the inlet capillary 2. In FIG. 1, the capillary gap bridge 11 is shown together with a dispenser 4 carrying a droplet of a sample 5 at the dispensing end 10. The droplet of the sample 5 is then dispensed into the capillary gap bridge 11 of buffer liquid in accordance with a first embodiment of the method according to the invention, which is described in the with the aid of FIG. 5-FIG. 8, or in accordance with a second embodiment of the method according to the invention, which is described with the aid of FIG. 9-FIG. 13.

Figure 7:
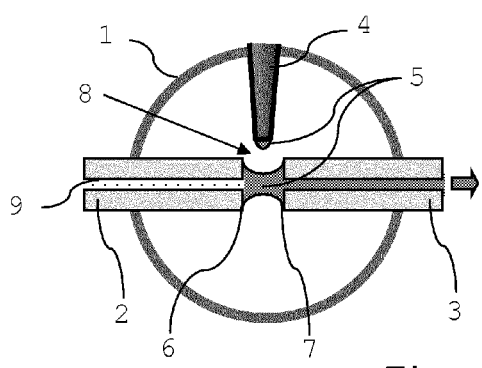
FIG. 7 shows the embodiment of the system of FIG. 5 and FIG. 6 after the sample has been dispensed into the capillary gap bridge.
Figure 8:
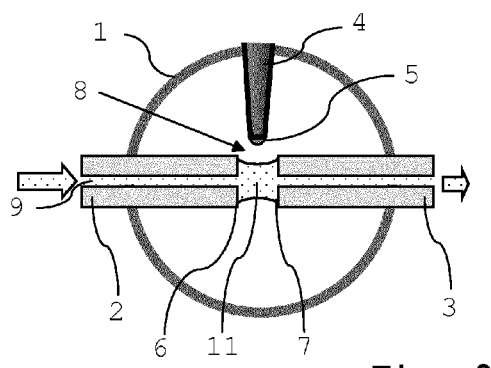
FIG. 8 shows a side view of the embodiment of the system of FIG. 4 with the dispenser being removed from the pressure chamber after the sample has been discharged from the outlet capillary, and with the capillary gap bridge of buffer liquid spanning the capillary gap again.

In FIG. 5-FIG. 8 the dispensing of a droplet of the sample 5 through the dispensing end 10 of a dispenser 4 into the capillary gap bridge 11 of buffer liquid is shown. As can be seen, the capillary gap bridge 11 is slightly constricted at the time of dispensing the droplet into the capillary gap bridge 11 relative to the capillary gap bridge 11 of buffer liquid at the time when no sample liquid is dispensed (see FIG. 1 or FIG. 8). The dispenser 4 is arranged such that the dispensing end 10 is arranged above the capillary gap 8 with the capillary gap bridge 11 of buffer liquid spanning the capillary gap 8 between the outlet end 6 of the inlet capillary 2 and the inlet end 7 of the outlet capillary 3, see FIG. 5. As the sample 5 is dispensed into the buffer liquid of the capillary gap bridge 11, see FIG. 6, a liquid bridge is formed between the sample 5 at the dispensing end 10 of dispenser 4 and the buffer liquid of the capillary gap bridge 11, see FIG. 6. The sample liquid 5 is then drawn in into the outlet capillary tube 3, as this is shown in FIG. 7. Once the sample liquid has been completely discharged from the outlet capillary 3, the capillary gap bridge 11 of buffer liquid 9 is re-established, and the dispensing end is removed from pressure chamber 1, see FIG. 8. The next sample liquid can then be dispensed into the capillary gap bridge 11 of buffer liquid as this is described above.

Figure 9:
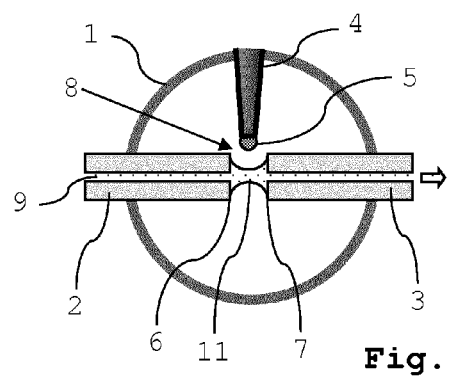
FIG. 9 shows the embodiment of the system of FIG. 5 at the beginning of the dispensing of the sample into inlet of the outlet capillary in accordance with a second embodiment of the method according to the invention.
Figure 10:
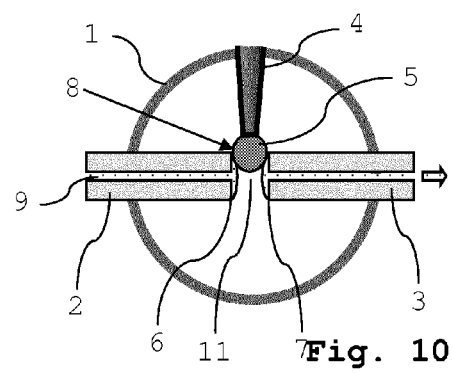
FIG. 10 shows the embodiment of the system of FIG. 9 during dispensing of the sample.
Figure 11:
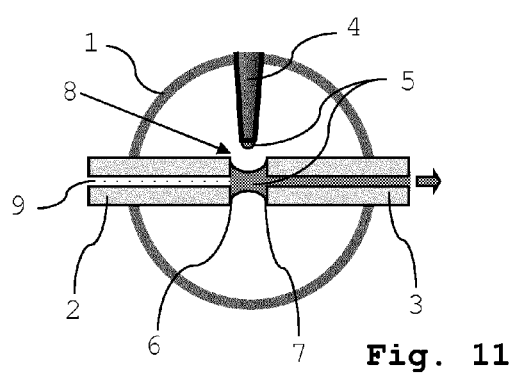
FIG. 11 shows the embodiment of the system of FIG. 9 and FIG. 10 after the sample has been dispensed and after the capillary gap bridge has been re-established, the capillary gap bridge being formed by the sample.
Figure 12:
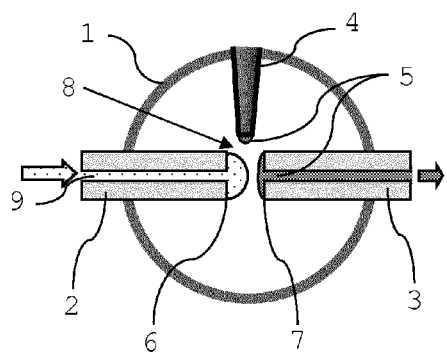
FIG. 12 shows the embodiment of the system shown in FIG. 9-FIG. 11, during discharge of the sample through the outlet capillary, and with the capillary gap bridge being interrupted again.
Figure 13:
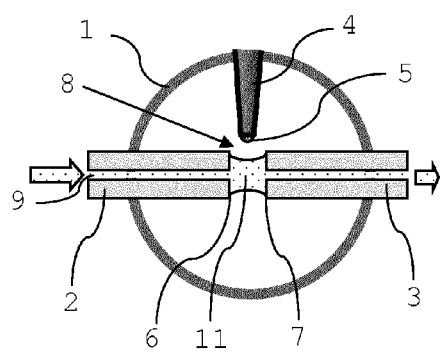
FIG. 13 shows the embodiment of the system shown in FIG. 9-FIG. 12 after the sample has been discharged from the outlet capillary, and after a capillary gap bridge of buffer liquid has been re-established.

In FIG. 9-FIG. 13 show the dispensing of a sample 5 through the dispensing end 10 of the sample dispenser 4 in accordance with a second method in which the capillary gap bridge 11 of buffer liquid spanning the capillary gap 8 is not continuously maintained. As shown in FIG. 9, the starting scenario is similar to that of the method described above, see also FIG. 5. However, the supply of buffer liquid 9 through the inlet capillary 2 is then substantially reduced so that the capillary gap bridge 11 of buffer liquid is discontinued. As a consequence, only two droplets remain at the outlet end 6 of the inlet capillary 2 and at the inlet end 7 of the outlet capillary 3. The sample 5 is dispensed into the capillary gap 8, see FIG. 10, so that either the sample 5 forms the capillary gap bridge, see FIG. 11, or the sample 5 forms a bridge with the droplet at the inlet end 7 of the outlet capillary 3, so that no capillary gap bridge of sample liquid 5 is established, see FIG. 12. In either case, the sample is subsequently discharged from the outlet capillary 3 as a consequence of the pressure difference between the overpressure in the pressure chamber 1 and the pressure outside the outlet capillary 3. Thereafter, the supply of buffer liquid is increased again so that a capillary gap bridge 11 of buffer liquid spanning the capillary gap 8 is formed again, as this is shown in FIG. 13.

Figure 14:
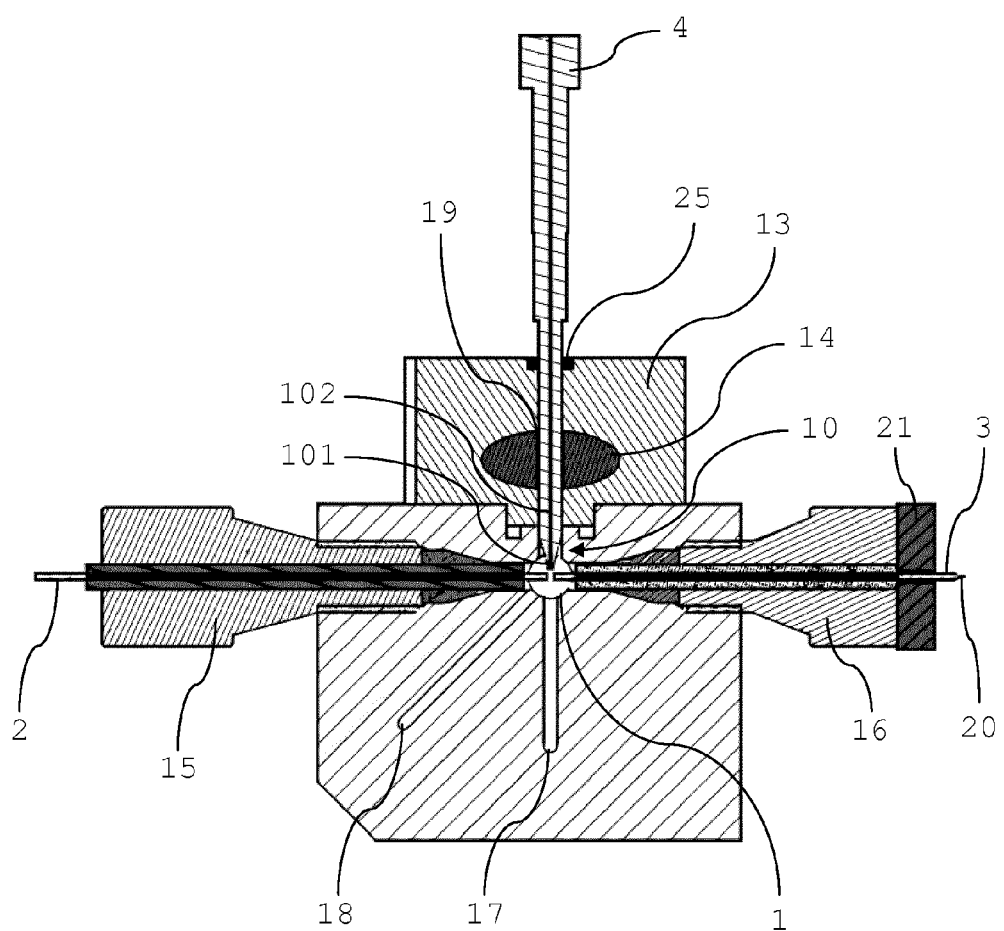
FIG. 14 shows a sectional view of a further embodiment of the system according to the invention.

FIG. 14 shows a further embodiment of the system according to the invention. The embodiment of the system shown in FIG. 14 comprises a pressure chamber 1 within a block-like housing, in which the outlet end of an inlet capillary 2 and the inlet end of an outlet capillary 3 are arranged aligned with each other. The capillary gap is formed between the outlet end of the inlet capillary 2 and the inlet end of the outlet capillary 3. Alignment of the outlet end of the inlet capillary 2 and the inlet end of the outlet capillary 3 is achieved with the aid of an inlet capillary holder 15 and an outlet capillary holder 16, respectively. Both the inlet capillary holder 15 and the outlet capillary holder 16 are screwed into corresponding threaded holes of the block-like housing. With the inlet capillary holder 15 and the outlet capillary holder 16 a positioning of the outlet end of the inlet capillary 2 and the inlet end of the outlet capillary 3 can be achieved in which the axes of the inlet capillary 2 and the outlet capillary 3 are aligned, for example with an accuracy of +/−0.02 mm to +/−0.1 mm. Also, the axial distance between the outlet end of the inlet capillary 2 and the inlet end of the outlet capillary 3 can be adjusted with the aid of inlet capillary holder 15 and outlet capillary holder 16.

A dispenser 4, e.g. a solid pin, pipette or any other suitable device, extends into the pressure chamber 1 for dispensing a sample through the dispensing end 10 of the dispenser 4, as this has been described above. The dispenser further comprises a channel 102 and a dispensing opening 101 arranged at the dispensing end 10. The dispensing opening 101 is in communication with the channel 102 to allow for dispensing of the sample through the dispensing opening 101. Optionally, the channel may be filled with a chromatographic material.

The dispenser 4 extends through a pressure-tight sample port 13 which comprises a locking member 14 having a passage extending through the locking member 14 to allow the dispenser 4 with the dispensing end to be moved into and out of the pressure chamber 1. The locking member 14 is movable. In the embodiment shown in FIG. 14, the locking member 14 may be moved into or out of the drawing plane by pulling or pushing the locking member 14. Thus, the locking member 14 is movable between a first position, in which the passage 19 is arranged as shown in FIG. 14 and in which it allows the dispenser 4 to pass through the passage 19 into the pressure chamber 1, and a second position, in which the passage 19 is arranged at a position in which it does not allow the dispenser 4 to pass through passage 19 due to the locking member having been pushed or pulled so that the passage 19 has been moved into or out of the drawing plane. In this second position, the locking member 14 locks the pressure chamber 1 in a pressure-tight manner. Alternatively, a locking member having a circular cross-section can be used (not shown in FIG. 14). Such locking member can then be moved by rotating the locking member between the first position and the second position. Any other type of locking member may also be used, of course.

After the sample is dispensed, the dispenser 4 can be removed until the end of the dispenser 4 has been retracted through the passage 19 but still penetrates through the seal 25. The locking member 14 can then be pushed or pulled in order to be moved to the second position in which it closes the pressure chamber 1. Thereafter, the dispenser 4 can be fully retracted through the seal 25 while the pressure chamber 1 is locked in a pressure-tight manner. Insertion of the dispenser 4 is to be performed the other way round. The dispenser 4 has to be inserted through the seal 25, however, only to an extent that the end of the dispenser is arranged above the locking member 14. Locking member 14 is then moved to the first position in which the passage 19 allows the dispenser to be moved therethrough and into the pressure chamber 1, so that the dispenser is arranged in the position shown in FIG. 14.

In case any sample inadvertently remains in the pressure chamber or falls down due to gravity, such liquid can be discharged from the pressure chamber 1 by means of a closable drain 17, which is arranged in fluid communication with the pressure chamber 1. In the embodiment of FIG. 14, drain 17 is arranged at the bottom of the block-like housing.

A pressure supply channel 18 is also shown in FIG. 14 which is in fluid communication with the pressure chamber 1. Also, it is desirable that a pressure drain (not shown in FIG. 14) is arranged in fluid communication with the pressure chamber 1. This pressure drain may comprise a discharge channel and a discharge valve which together form a well-defined pressure leak which may facilitate the control and maintenance of a constant pressure within the pressure chamber 1.

Typical dimensions of the inlet capillary 2 and of the outlet capillary 3 may be an inner diameter in the range of about 5 µm to 50 µm and an outer diameter in the range of 50 µm to 500 µm, the ranges explicitly including the boundary values. It goes without saying that the respective outer diameter of a capillary is always larger than the respective inner diameter of the same capillary. The length of the outlet capillary 3 may be in the range of 10 mm to 50 mm.

In the embodiment shown in FIG. 14 the outlet capillary 3 has a tapered outlet end 20. The outer surface of the outlet capillary 3 is provided with metal (for example it may be metallized) to form an electrical contact. This metal surface must be electrically isolated against the pressure chamber 1 and against the outlet capillary holder 16. A voltage electrode 21 is arranged in electrical contact with the metallized outer surface to form an electrical contact to the outlet end 12 of the outlet capillary 3. Voltage electrode 21 has an electrical potential with respect to an adjacent counter electrode (not shown) so that electrospraying of the liquid through the outlet end 20 of outlet capillary 3 into a mass spectrometer is possible.

Figure 15:
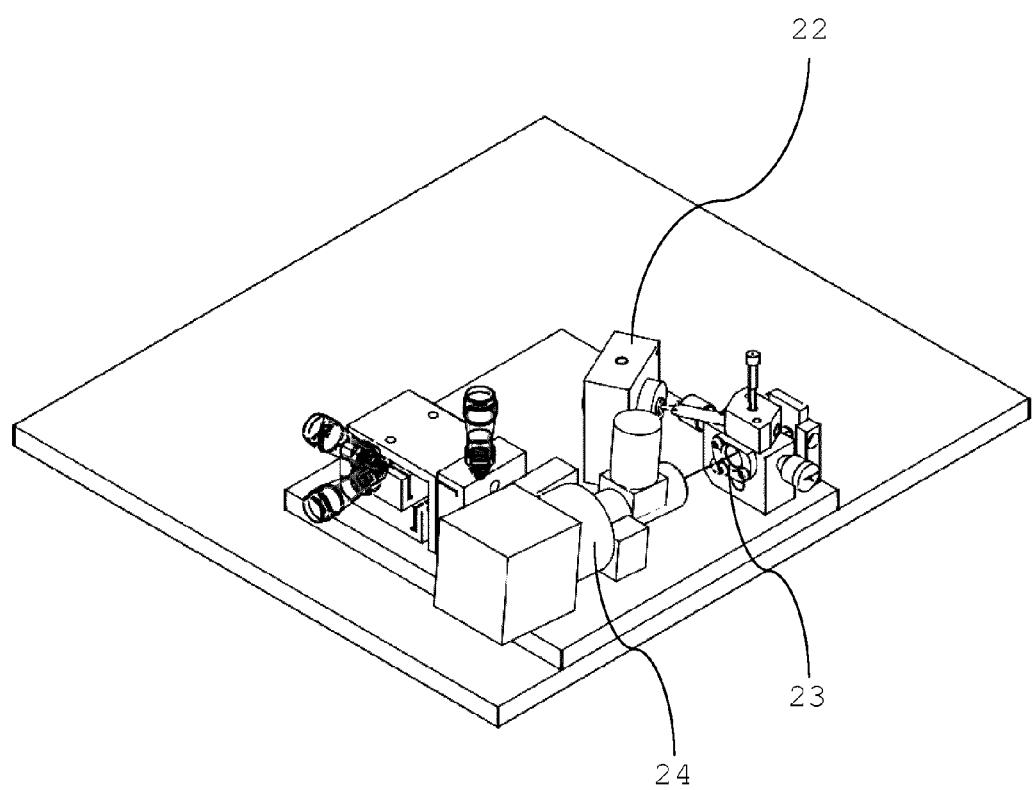
FIG. 15 shows a perspective view of a further embodiment of the system according to the invention.

FIG. 15 shows a further embodiment of the system according to the invention in which the pressure chamber 1 comprises a window 23 which is arranged such that the outlet end of the inlet capillary, the inlet end of the outlet capillary, the dispensing end of the dispenser, and the capillary gap are visible by a camera 24. With the aid of camera 24 an image of the ends of the inlet capillary and of the outlet capillary as well as of the capillary gap and of the liquid capillary gap bridge can be taken. A control unit may control the flow of buffer liquid through the inlet capillary tube before, during, and after dispensing of the sample on the basis of an image analysis. Also, adjustments of the ends of the inlet capillary and the outlet capillary relative to each other can be performed using image analysis. Still further, the position of the end of the dispenser at the capillary gap can be controlled using image analysis. Finally, the motor 22 for moving the locking member can be controlled using image analysis.

Embodiments of the invention have been described with the aid of the drawings. However, various modifications and changes to the described embodiments are possible without departing from the general teaching underlying the invention. Therefore, the invention is not to be understood as being limited to the described embodiments, but rather the scope of protection is defined by the appended claims.

The invention claimed is:

1. A system for dispensing a sample, in particular a liquid sample, into a buffer liquid, the system comprising:
    a pressure chamber having pressure supply means for generating an overpressure within the pressure chamber relative to a pressure outside the pressure chamber,
    an inlet capillary for supplying a buffer liquid to an outlet end of the inlet capillary, the outlet end of the inlet capillary being arranged in the pressure chamber,
    an outlet capillary for discharging the buffer liquid and/or the sample from the pressure chamber, the outlet capillary having an inlet end being arranged in the pressure chamber in a manner such that the outlet end of the inlet capillary and the inlet end of the outlet capillary are facing each other to form a capillary gap allowing the buffer liquid exiting the outlet end of the inlet capillary to cross the capillary gap and enter the inlet end of the outlet capillary and
    a dispenser having a dispensing end which, during dispensing of the sample, is arranged in the pressure chamber at the capillary gap to allow the sample to be dispensed from the dispensing end into the buffer liquid entering the inlet end of the outlet capillary,
        wherein the pressure chamber comprises a pressure-tight sample port adapted to allow the dispenser with the dispensing end to be moved into and out of the pressure chamber.

2. A system according to claim 1, wherein the pressure-tight sample port comprises a locking member having a passage therethrough, the locking member being movable between a first position in which the passage is arranged to allow the dispenser to pass into the pressure chamber and a second position in which the locking member locks the pressure chamber in a pressure-tight manner.

3. A system according to claim 1, wherein the dispenser comprises a channel and a dispensing opening arranged at the dispensing end and being in communication with the channel to allow for dispensing of the sample through the dispensing opening.

4. A system according to claim 1, further comprising an inlet capillary holder and an outlet capillary holder for positioning the outlet end of the inlet capillary and the inlet end of the outlet capillary aligned with one another within the pressure chamber, in particular with an accuracy in the range of +/−0.02 mm to +/−0.1 mm.

5. A system according to claim 1, wherein the pressure chamber comprises a window which is arranged such that the outlet end of the inlet capillary, the inlet end of the outlet capillary, the dispensing end of the dispenser, and the capillary gap are visible.

6. A system according to claim 5, further comprising a camera for taking an image of at least the capillary gap, and a control unit adapted to analyze the image taken by the camera to automatically control the pressure supply means and/or the flow of buffer liquid through the inlet capillary.

7. A system according to claim 1, wherein the pressure chamber comprises a closable drain arranged in fluid communication with the capillary gap.

8. A system according to claim 1, wherein the pressure supply means comprises an overpressure source, a supply channel which is in fluid communication with the overpressure source and the pressure chamber for introducing a pressurized gas into the pressure chamber, and a pressure drain for allowing pressurized gas to be discharged from the pressure chamber, the pressure drain comprising a discharge channel and a discharge valve, the discharge channel being in fluid communication with the pressure chamber and the discharge valve to establish a constant difference between the pressure within the pressure chamber and the pressure outside the pressure chamber, in particular a difference in pressure between 0.5 bar and 5 bar.

9. A system according to claim 1, wherein the inlet capillary and the outlet capillary have an inner diameter in the range of 5 μm to 100 μm and an outer diameter in the range of 50 μm to 500 μm.

10. A system according to claim 1, wherein the outlet capillary comprises at least one inner surface section of a material to allow for the adsorption and desorption of the sample.

11. A system according to claim 1, wherein the outlet capillary has a length in the range of 10 mm to 50 mm.

12. A system according to claim 1, wherein the inlet capillary and/or the outlet capillary is made from a fused silica, glass or polytetrafluoroethylene.

13. A system according to claim 1, further comprising:
an outlet capillary holder for holding the outlet capillary, wherein the outlet capillary has a tapered outlet end,
the outlet capillary at least at the tapered outlet end is provided on its outer surface with metal,
the outlet capillary further being electrically isolated against the pressure chamber and the outlet capillary holder, respectively, and
the system further comprising a voltage electrode arranged in electrical contact with the tapered outlet end of the outlet capillary for applying a voltage to the metal provided on the outer surface of the outlet capillary at the tapered outlet end.

14. A method for dispensing a sample into a buffer liquid, the method comprising the steps of:
providing a system for dispensing a sample according to claim 1,
generating an overpressure within the pressure chamber,
producing a buffer liquid flow through the outlet end of the inlet capillary into the inlet end of the outlet capillary,
controlling the overpressure within the pressure chamber such that the difference between the pressure in the pressure chamber and the pressure outside the pressure chamber is constant to establish a constant flow rate in the outlet capillary,
dispensing the sample through the dispensing end of the sample dispenser into the buffer liquid entering the inlet end of the outlet capillary.

15. A method according to claim 14, wherein
a capillary gap bridge of buffer liquid is continuously maintained between the outlet end of the inlet capillary and the inlet end of the outlet capillary and
the step of dispensing the sample through the dispensing end of the dispenser comprises dispensing the sample into the continuously maintained capillary gap bridge.

* * * * *